United States Patent [19]

Clapham

[11] Patent Number: 5,795,351
[45] Date of Patent: Aug. 18, 1998

[54] LASER REFRACTIVE SURGERY STATION

[75] Inventor: Terrance N. Clapham, Saratoga, Calif.

[73] Assignee: VISX, Incorporated, Santa Clara, Calif.

[21] Appl. No.: 752,662

[22] Filed: Nov. 19, 1996

[51] Int. Cl.⁶ .................................................. A61F 9/007
[52] U.S. Cl. .................................. 606/4; 606/5; 351/221
[58] Field of Search ........................... 606/4, 5; 351/200, 351/214, 222, 245

[56] References Cited

U.S. PATENT DOCUMENTS

| | | |
|---|---|---|
| 3,703,176 | 11/1972 | Vassiliadis et al. . |
| 3,720,213 | 3/1973 | Hobart et al. . |
| 3,828,788 | 8/1974 | Krasnov et al. . |
| 4,520,816 | 6/1985 | Schachar et al. . |
| 4,554,917 | 11/1985 | Tagnon . |
| 4,561,436 | 12/1985 | Munnerlyn . |
| 4,638,801 | 1/1987 | Daly et al. . |
| 4,711,542 | 12/1987 | Ichihashi et al. . |
| 4,736,744 | 4/1988 | Koike et al. . |
| 4,759,360 | 7/1988 | Nakanishi et al. . |
| 4,848,340 | 7/1989 | Bille et al. . |
| 5,098,426 | 3/1992 | Sklar et al. . |
| 5,116,114 | 5/1992 | Nakamura et al. . |
| 5,226,903 | 7/1993 | Mizuno . |
| 5,425,729 | 6/1995 | Ishida et al. . |
| 5,442,487 | 8/1995 | Mizuno . |
| 5,634,920 | 6/1997 | Hohla .................................. 606/12 |

*Primary Examiner*—Michael Peffley
*Assistant Examiner*—Roy D. Gibson
*Attorney, Agent, or Firm*—Townsend and Townsend and Crew LLP

[57] ABSTRACT

A surgery station is provided for refractive eye surgery by laser photoablation, with the patient in a normal and comfortable upright seated position. The surgery station comprises a head support unit for retaining the head of the seated patient in a fixed position relative to an optical examination instrument such as an operating microscope, and further with respect to a laser beam for performing refractive surgery by corneal photoablation.

17 Claims, 3 Drawing Sheets

5,795,351

LASER REFRACTIVE SURGERY STATION

BACKGROUND OF THE INVENTION

This invention relates generally to surgery apparatus and systems for performing laser refractive eye surgery. More specifically, this invention relates to an efficient and economical surgery station adapted for performing refractive surgery by corneal photoablation, with a physician-patient interface that is more convenient to the doctor and less threatening to the patient.

Refractive eye surgery has undergone significant advances in recent years, with the result that refractive surgery has been successfully demonstrated and approved for correcting vision errors particularly such as myopia (near-sighted). Such refractive surgery has the capability to restore normal, substantially 20/20 uncorrected vision, so that a patient is no longer required to wear corrective eyeglasses or contact lenses. Surgical restoration of normal uncorrected sight has tremendous potential in terms of overall lifestyle, long range cost, and convenience to millions of patients suffering from near-sightedness and other vision defects including, but not limited to hyperopia (far-sighted), astigmatism, etc. Restoration of normal sight additionally opens numerous occupational opportunities, such as police and firefighting, to persons who would not otherwise meet vision criteria.

Radial keratotomy (RK) is one refractive surgery technique which has been practiced in the United States for the past few decades. In radial keratotomy a series of precision radial incisions are formed in the peripheral cornea to selectively and controllably weaken the cornea such that the normal intraocular pressure causes the peripheral cornea to push outwardly. This results in a relative flattening of the central optical zone of the cornea. This technique has proven effective to correct mild myopia, with the degree of correction being a function of the incision number and depth. However, concern regarding the long term stability of the incised cornea, especially in response to an impact blow to the head, has been a deterrent to the use of radial keratotomy as a routine vision correction procedure.

More recently, photorefractive keratectomy (PRK) has been developed and approved for use in the United States as a refractive surgery procedure. In photorefractive keratectomy, an excimer laser source is used to reshape the outer or anterior surface of the cornea by photoablation, substantially without significant weakening of the corneal structure. Photorefractive keratectomy can be used to correct a significant range of myopic conditions by flattening the central optical zone of the cornea, or to correct hyperopia by reshaping the perimeter region of the cornea relative to the central optical zone. This technique (PRK) is rapidly becoming the preferred method of performing refractive eye surgery, with one commercial excimer laser system being marketed under the name Star by VISX, Incorporated of Santa Clara, Calif.

Photorefractive keratectomy (PRK) requires removal of the epithelium layer in the central optical zone to be reshaped by laser photoablation. Removal of the epithelium layer has been accomplished by scraping with a blunt edge spatula, although improved epithelium debridement brushes have recently become available and computer controlled laser techniques for epithelium removal are under development. Following epithelium removal to expose the cornea, the excimer laser is carefully aligned with the patient's eye and then operated in a precision and computer controlled manner to reshape the anterior surface of the cornea by photoablation, wherein corneal cells are removed to reshape the anterior surface in a custom manner to correct the refractive errors for the specific patient. Following the surgery, a bandage contact lens is normally placed on the eye for a few days during which the epithelium is allowed to heal.

Current PRK surgical techniques and systems require the epithelium removal and the laser photoablation steps to be performed while the patient is laying down or reclined in a supine position. In this regard, current techniques and devices for epithelium removal have essentially restricted the procedure to a supine patient orientation in order to provide a conventional physician-patient surgical interface which is both familiar and comfortable to the doctor.

Since it is extremely important to perform the laser photoablation step substantially immediately after epithelium removal, prior to any significant corneal drying, the laser surgery step has also been performed with the patient remaining in the supine position. Unfortunately, however, this doctor-patient interface with the patient in a supine position can be extremely threatening and intimidating to the patient. Moreover, this supine orientation requires the doctor to procure an appropriate operating table or special reclinable chair in order to perform laser refractive surgeries, thereby increasing the requisite equipment cost and resultant cost of the surgery to the patient.

The present invention is directed to an improved surgery station for performing laser refractive eye surgery, wherein the patient is oriented in a comfortable and relatively non-threatening upright seated position.

SUMMARY OF THE INVENTION

In accordance with the invention, an improved laser refractive surgery station is provided for performing photorefractive eye surgery by laser photoablation with the patient oriented in a normal and comfortable upright seated position. The surgery station comprises a head support unit for supporting and retaining the head of a seated patient in a fixed and predetermined position relative to an optical examination instrument such as an operating microscope. The optical examination instrument is in turn coupled with a laser unit including a laser light source and related control means for producing a precision controlled laser beam that is aligned via the optical examination instrument with the patient's eye to perform the photorefractive surgery.

In one preferred form, the surgery station comprises a base frame such as a table having the head support unit mounted thereon, wherein the head support unit typically includes an adjustable chinrest and/or related forehead rest in a position to support and retain the head of a patient seated on a conventional chair. The head support unit orients the patient's head relative to the optical examination instrument to enable the physician to examine the left or right eye of the patient, preferably with the physician seated relative to the base frame in a position opposite to the patient. With this doctor-patient interface, surgical preparation can be performed quickly and easily, including anesthetizing the patient's eye and removing the epithelial layer from a central optical zone thereof by known epithelium removal techniques.

The optical examination instrument is movably supported on the base frame to accommodate accurate alignment with the patient's eye. The examination instrument is optically coupled by an array of mirrors to the laser unit to deliver the controlled laser beam to the patient's eye to perform the corneal photoablative surgery. In this regard, the laser control means includes appropriate control elements mounted on the base frame in a position accessible to the physician to enable accurate and facilitated control over the surgical procedure.

In one alternative form, the surgery station includes the head support unit and related optical examination instrument mounted on a base frame in the form of an upright support pole or the like, for swinging movement relative to a traditional opthamologic examination chair. In this embodiment, the laser unit and related control elements are situated on or adjacent to the base frame, with appropriate mirror means or the like for optically coupling the laser beam to the examination instrument.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
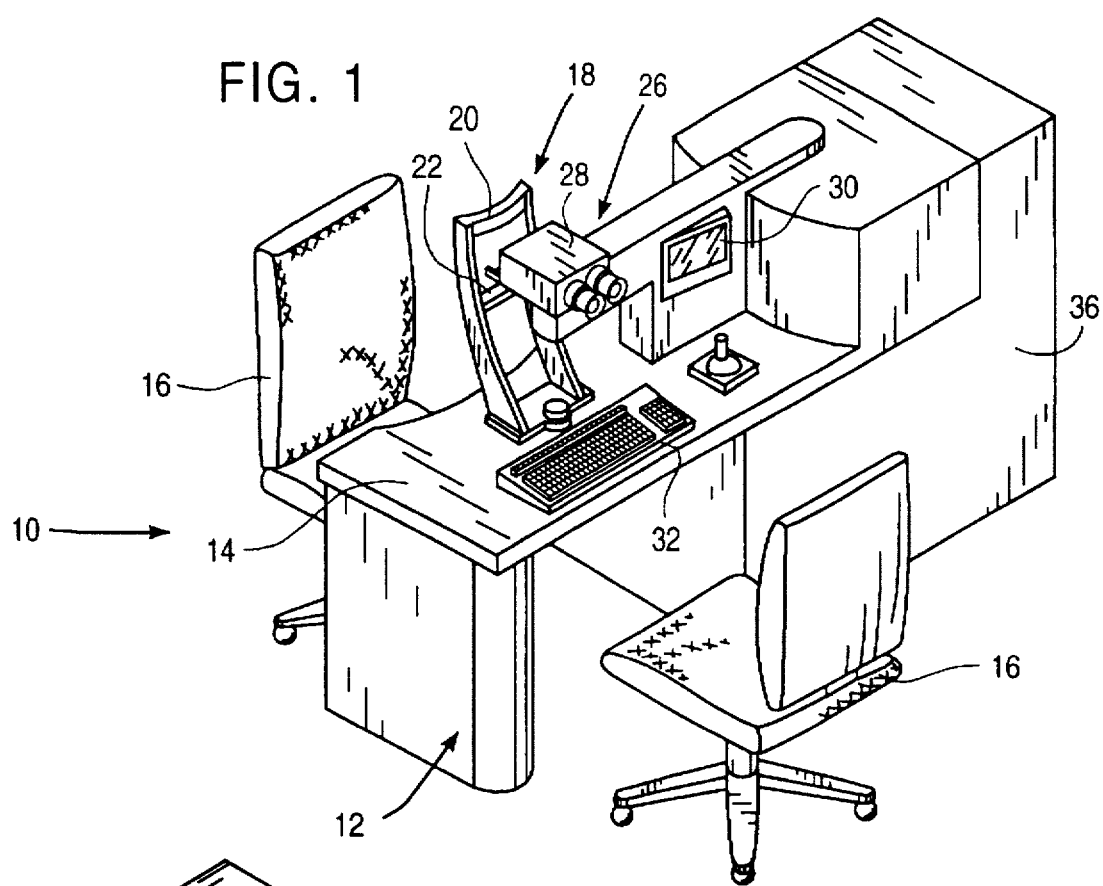
FIG. 1 is a front perspective view illustrating an improved laser photorefractive surgery station embodying the novel features of the invention.

As shown in the exemplary drawings, a laser photorefractive surgery station referred to generally by the reference numeral 10 is provided for performing refractive eye surgery by corneal photoablation. The surgery station 10 is designed to orient the patient in an upright seated position which is more convenient to the doctor and less threatening to the patient.

The photorefractive surgery station 10 of the present application is specifically designed to perform photorefractive keratectomy (PRK) by which an excimer laser of particular wavelength and power is used to reshape the anterior surface of the cornea to correct refractive vision errors. The excimer laser is applied to a central optical zone of the cornea and functions to remove corneal cells by photoablation, to restore substantially normal uncorrected vision to the patient. PRK has been used effectively to reshape the cornea by flattening the central optical zone to correct a myopic (near-sighted) condition, or to reshape a peripheral region of the optical zone to increase the corneal curvature to correct a hyperopic (far-sighted) condition. One commercial excimer laser system for performing PRK surgeries is available from VISX, Incorporated of Santa Clara, Calif. under the name Star.

In general terms, the surgery station 10 of the present invention is designed to facilitate PRK surgeries in an economical yet precision controlled and safe manner, with the patient beneficially oriented in an upright seated position which is relatively nonthreatening. The surgery station 10 permits the entire refractive surgery procedure to be performed with both the patient and the physician disposed in a comfortable and substantially normal seated upright interface. The station 10 further accommodates use in combination with conventional and/or existing seating apparatus of the type commonly present in an opthamologist's office, thereby reducing or minimizing the need for special and costly equipment dedicated to refractive surgery use, and the need for dedicated floor space attributable to such equipment. As a result, the present invention effectively reduces the cost of PRK surgeries and thereby advantageously expands the availability of PRK surgery to a wider range of prospective patients.

Figure 2:
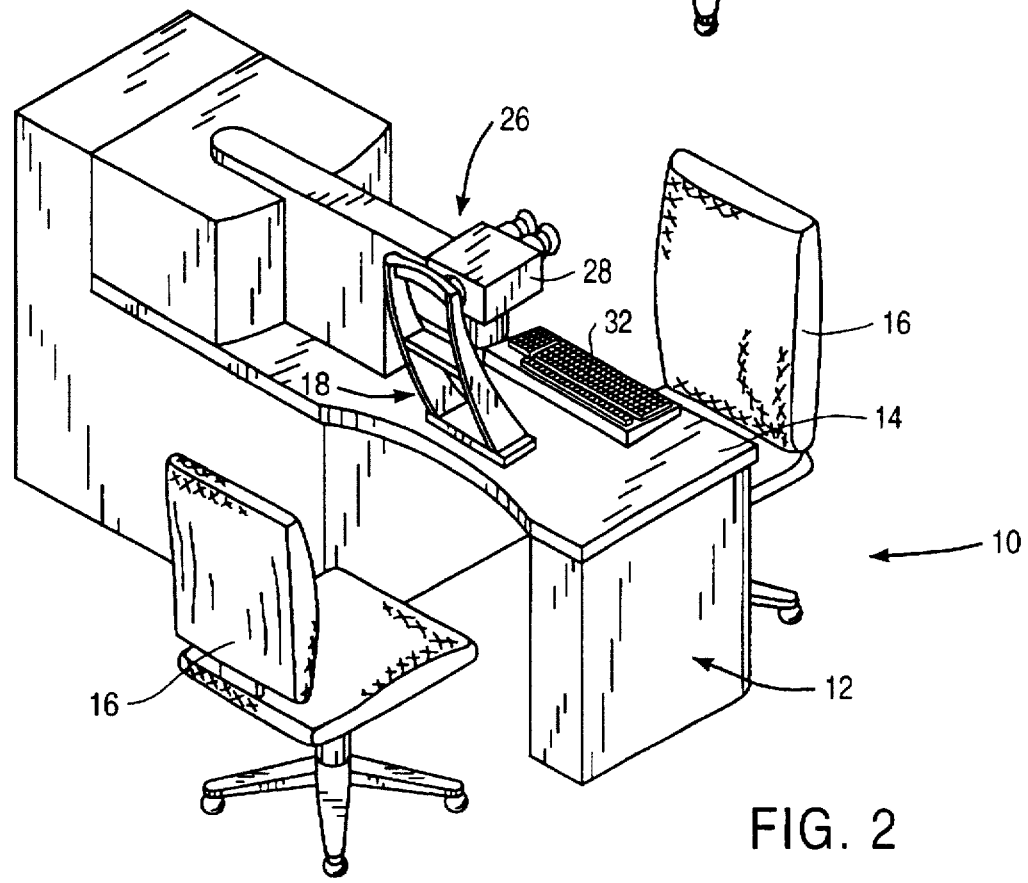
FIG. 2 is a rear perspective view of the surgery station shown in FIG. 1.

FIGS. 1 and 2 show the surgery station 10 in one preferred form to include a base frame 12 in the form of a simple table having a top 14 adapted for seated reception of a patient and a doctor on opposite sides thereof, wherein both individuals are seated on conventional chairs 16. An adjustable head support unit 18 is mounted on a patient side of the table 12 and includes a forehead rest 20 in combination with a conventional chinrest 22 which is adjustable and preferably motorized for supporting and retaining the patient's head 24 (FIG. 3) in a fixed position relative to the table. An optical examination instrument 26 such as an operating microscope or slit lamp includes a viewer 28 mounted on the base frame 12 at the doctor side of the table for use by the physician during preparation for and performance of the refractive surgery. A computer screen 30 and related keyboard control panel 32 are also provided on the base frame, in association with the examination instrument 26, for appropriate use by the physician.

Figure 4:
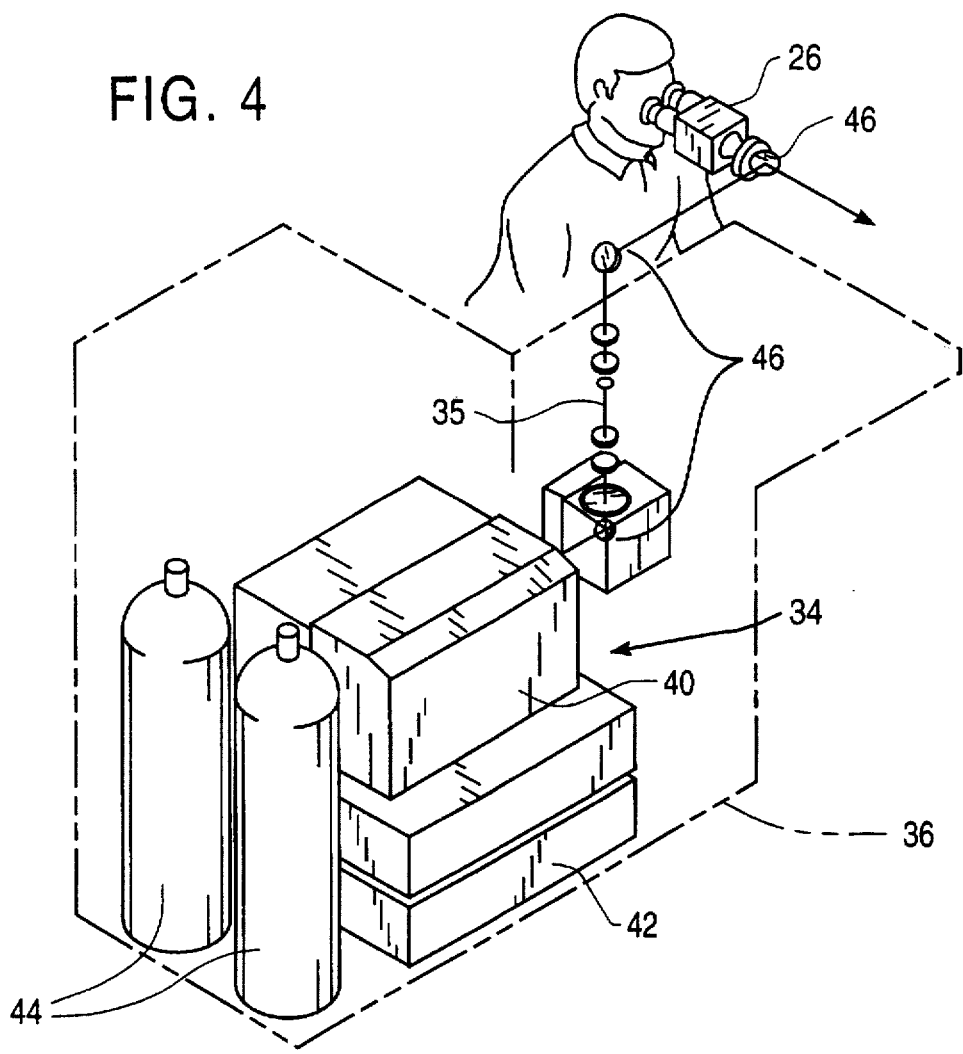
FIG. 4 is a schematic diagram depicting optical coupling of a laser unit with an optical examination instrument.

A laser unit 34 (FIG. 4) is mounted on the base frame 12 or in fixed relation thereto, such as by installing the laser unit 34 as part of a cabinet 36 forming a portion of the table. As shown, the laser unit 34 comprises an excimer laser 40 with appropriate electronic modules 42 and gas supply canisters 44, for generating a laser beam used to perform the refractive surgery. A typical excimer laser for photoablation of the anterior surface of the cornea produces an ultraviolet beam having a wave length in the range of about 180–215 nanometers, and preferably about 200 nanometers. An example of such excimer laser is an argon fluoride laser which produces a beam of light having a wave length of about 193 nanometers.

The laser light beam is reflected by an appropriately positioned array of mirrors 46 (FIG. 4) mounted on the base frame 12 to couple the laser beam to the optical examination instrument 26, which in turn controllably redirects the beam to the patient's eye to perform the photoablative surgery. Importantly, by use of the surgery station 10 of the present invention, the surgery can be performed quickly and easily, and without placing the patient in a threatening position or environment.

Figure 3:
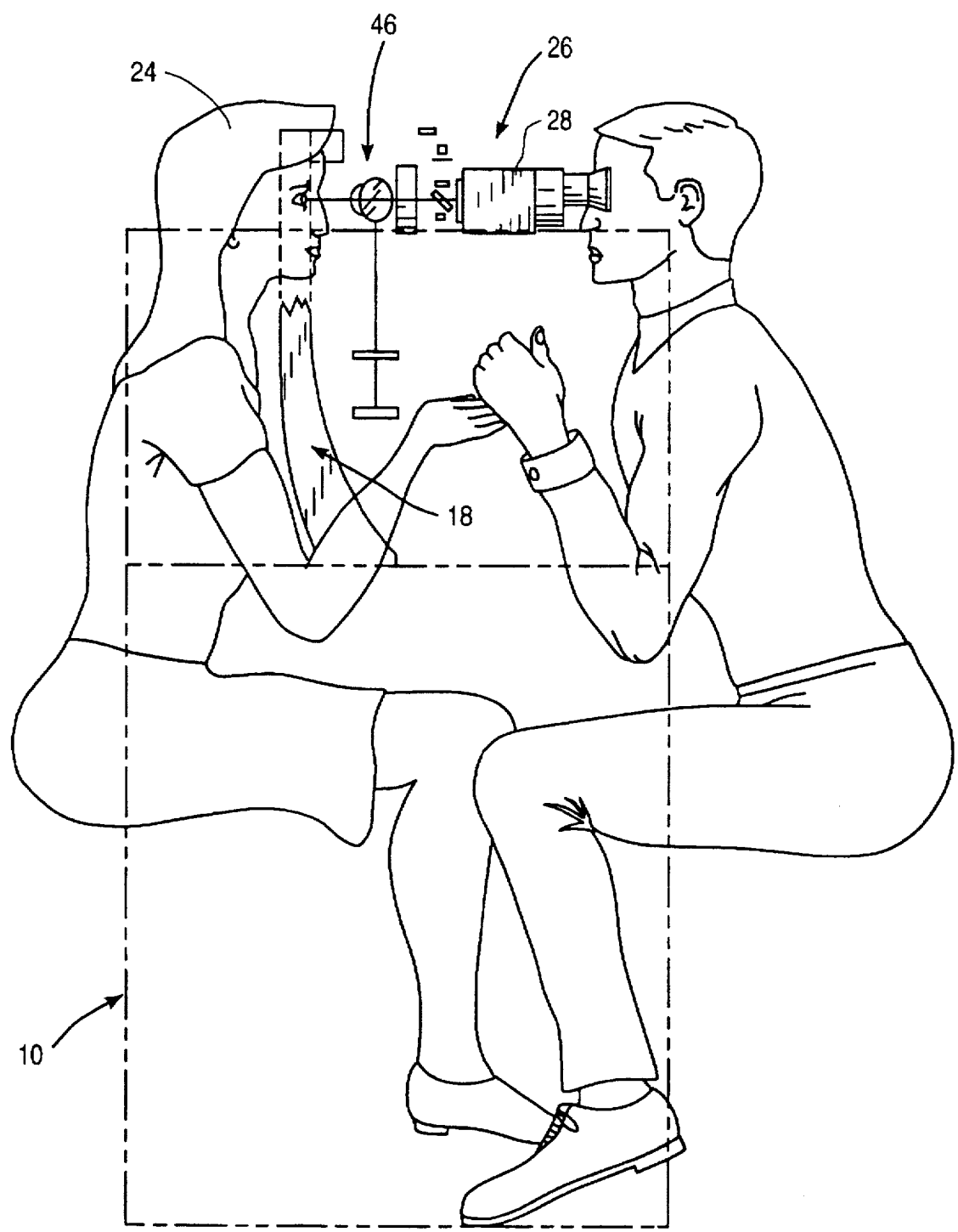
FIG. 3 is a schematic side elevational view showing the doctor-patient interface upon use of the improved surgery station.

More particularly, the surgery station is used as follows. The patient is positioned on the patient side of the table 12 in a normal upright seated position using a conventional chair 16 (FIG. 3). The patient's eye to be operated on is anesthetized by appropriate drops, and the patient's head 24 is then positioned in a predetermined manner by means of the head support unit 18. The physician, also seated on a conventional chair 16, can then proceed to remove the epithelium in a central optical zone of the cornea in order to expose the underlying corneal tissue for laser photoablation. Removal of the epithelium is performed while the patient is seated, by use of a blunt edge spatula or an epithelial debridement brush. Alternately, the laser unit 34 can be aligned with the patient's eye to permit laser removal of the epithelium.

In this regard, such alignment of the laser unit 34 with the patient's eye is accomplished by appropriate sliding or motor-driven adjustment of the viewer 28 of the optical examination instrument 26 preparatory to epithelium removal, so that the examination instrument 26 can be used by the physician during the epithelium removal step. When the epithelium removal is complete, the patient is already pre-positioned and pre-aligned with the laser unit 34 so that the photoablative surgery can proceed virtually immediately without needing to move the patient or otherwise to align laser devices with the patient's eye. Immediate performance of the laser surgery, as soon as possible following epithelium removal, enhances the accuracy of the photoablative process since there is no significant opportunity for the exposed corneal tissue to dry out before surgery. In addition, with the patient seated in the upright position, it is believed that photoablated material removal from the cornea will fall away from the patient's eye and not interfere with the surgical process, whereby improved vision correction results can be obtained.

Following the surgery, the patient's eye is typically covered with a bandage contact lens for a few days during which the epithelium layer begins to reform and heal.

Figure 5:
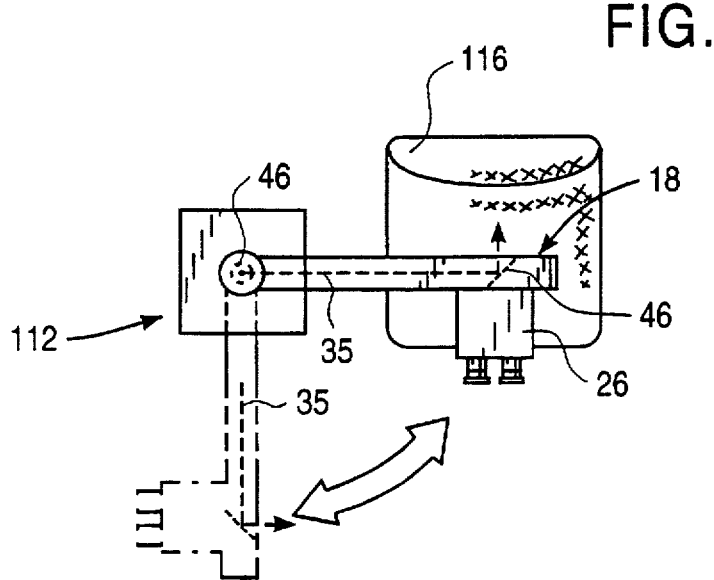
FIG. 5 is a schematic view illustrating an alternative preferred form of the invention.

FIG. 5 shows an alternative preferred form of the invention, wherein a modified patient chair 116 is provided in the form of a conventional patient examination chair of the type found in a typical opthamologist's office. A modified base frame 112 is mounted adjacent to the chair 116 and supports the head support unit 18 together with the optical examination instrument 26. FIG. 5 shows the base frame 112 in the form of a support pole with the head support unit 18 and the examination instrument 26 mounted on a movable frame means such as a swingaway arm adapted for swinging movement between an operative position in front of the patient chair 116 and an out-of-the-way position displaced away from the patient chair. The examination instrument 26 is again optically coupled to the laser unit 34 which can be securely mounted as part of a common structure with the support pole, or otherwise securely mounted in a fixed or known position adjacent to the support pole. The surgery station shown in FIG. 5 is used in the same manner as previously described with respect to the embodiment of FIGS. 1–4.

For both versions of the invention as shown, the patient is seated in a comfortable and minimally intimidating position throughout the entire surgical procedure. As a result, the PRK surgery can be performed rapidly and efficiently, virtually in a walk-in, walk-out fashion, without necessitating the additional time and equipment for preparing, positioning and aligning the patient in a supine orientation. Moreover, the upright seated system of the invention is highly compatible with existing patient-seated opthamologic examination procedures and equipment, to minimize the space and equipment costs to provide for PRK surgery.

A variety of further modifications and improvements to the invention will be apparent to those skilled in the art. Accordingly, no limitation on the invention is intended by way of the foregoing description and accompanying drawings, except as set forth in the appended claims.

What is claimed is:

1. A laser refractive surgery station, comprising:
    a base frame;
    a head support unit mounted on said base frame and including means for supporting and retaining the head of a patient seated in an upright position adjacent to said base frame;
    an optical examination instrument mounted on said base frame in a position for use by a physician in preparation for and performance of laser refractive surgery;
    a laser unit mounted in a predetermined fixed position relative to said base frame, said laser unit including means for generating a controlled power laser beam for corneal photoablation; and
    optic means for coupling said laser beam to said optical examination instrument for redirection thereby to an eye of the patient;
    wherein said base frame comprises a support pole mounted adjacent to an examination chair, and movable frame means on said support pole for movement between a first position generally in front of the examination chair and a second position displaced away from in front of the examination chair, said head support unit and said optical examination instrument being mounted on said movable frame means.

2. The laser refractive surgery station of claim 1 wherein said laser beam comprises an ultraviolet beam having a wave length in the range of from about 180 to about 215 nanometers.

3. The laser refractive surgery station of claim 2 wherein said laser beam has a wavelength of about 200 nanometers.

4. The laser refractive surgery station of claim 2 wherein said laser beam has a wavelength of about 193 nanometers.

5. The laser refractive surgery station of claim 1 wherein said laser unit beam generating means comprises an argon fluoride excimer laser.

6. The laser refractive surgery station of claim 1 wherein said optical examination instrument comprises an examination microscope.

7. The laser refractive surgery station of claim 1 wherein said optical examination instrument is mounted on said base frame for use by a physician in a seated upright position at one side of said base frame generally opposite to the seated patient.

8. A laser refractive surgery station, comprising:
    a base frame;
    a head support unit mounted on said base frame and including a head support adapted to restrain and support a head of a patient seated in an upright position adjacent to said base frame;
    an optical examination instrument mounted on said base frame in a position for use by a physician in preparation for and performance of laser refractive surgery;
    a laser unit mounted in a predetermined fixed position relative to said base frame, said laser unit including a laser to generate a controlled power laser beam for corneal photoablation; and
    optics coupling said laser beam to said optical examination instrument for redirection thereby to an eye of the patient;
    wherein said base frame comprises a support pole mounted adjacent to an examination chair, and a movable frame mounted on said support pole so as to move between a first position generally in front of the examination chair and a second position displaced away from in front of the examination chair, said head support unit and said optical examination instrument being mounted on said movable frame.

9. The laser refractive surgery of claim 8 wherein said movable frame comprises a swinging table.

10. A laser refractive surgery station, comprising:
    a base frame;

a patient chair at one side of said base frame for seated support of a patient in an upright seated position;

a head support unit for supporting and retaining the head of a patient seated in said patient chair in a predetermined position relative to said base frame;

a physician chair at a side of said base frame generally opposite to said patient chair;

an optical examination instrument mounted on said base frame in a position for use by a physician seated on said physician chair in preparation for and performance of laser refractive surgery on an eye of a patient seated in said patient chair;

a laser unit mounted in a predetermined fixed position relative to said base frame, said laser unit including means for generating a controlled power laser beam for corneal photoablation; and optic means for coupling said laser beam to said optical examination instrument for redirection thereby to an eye of the patient;

wherein said base frame comprises a support pole mounted adjacent to an examination chair, and movable frame means on said support pole for movement between a first position generally in front of the examination chair and a second position displaced away from in front of the examination chair, said head support unit and said optical examination instrument being mounted on said movable frame means.

11. The laser refractive surgery station of claim 10 wherein said laser beam comprises an ultraviolet beam having a wave length in the range of from about 180 to about 215 nanometers.

12. The laser refractive surgery station of claim 11 wherein said laser unit beam generating means comprises an argon fluoride excimer laser.

13. The laser refractive surgery station of claim 10 wherein said optical examination instrument comprises an operating microscope.

14. The laser refractive surgery station of claim 10 wherein said base frame comprises a table with said head support unit and said optical examination instrument mounted thereon in positions for interface with a patient and physician seated at opposite sides of said table.

15. The laser refractive surgery station of claim 14 wherein said base frame further includes a cabinet portion fixed to said table, said laser unit being mounted in said cabinet portion.

16. A laser refractive surgery station, comprising:

a base framer;

a patient chair at one side of said base frame for seated support of a patient in an upright seated position;

a head support unit for supporting and retaining the head of a patient seated in said patient chair in a predetermined position relative to said base frame;

a physician chair at a side of said base frame generally opposite to said patient chair;

an optical examination instrument mounted on said base frame in a position for use by a physician seated on said physician chair in preparation for and performance of laser refractive surgery on an eye of a patient seated in said patient chair;

a laser unit mounted in a predetermined fixed position relative to said base frame, said laser unit including a laser for generating a controlled power laser beam for corneal photoablation; and optic coupling said laser beam to said optical examination instrument for redirection thereby to an eye of the patient;

wherein said base frame comprises a support pole mounted adjacent to an examination chair, and a movable frame mounted on said support pole so as to move between a first position generally in front of the examination chair and a second position displaced away from in front of the examination chair, said head support unit and said optical examination instrument being mounted on said movable frame.

17. The laser refractive surgery station of claim 16 wherein said movable frame comprises a swinging table.

* * * * *